(12) United States Patent
Kango

(10) Patent No.: US 9,791,374 B2
(45) Date of Patent: Oct. 17, 2017

(54) MICRO-FLUIDIC SURFACE PLASMON RESONANCE CHIP

(71) Applicant: HITECH ANALYTICAL AND DIAGNOSTIC SOLUTIONS, LLC, Gaithersburg, MD (US)

(72) Inventor: Reyaz Kango, Gaithersburg, MD (US)

(73) Assignee: HITECH ANALYTICAL AND DIAGNOSTIC SOLUTIONS, LLC, Gaithersburg, MD (US)

( * ) Notice: Subject to any disclaimer, the term of this patent is extended or adjusted under 35 U.S.C. 154(b) by 0 days.

(21) Appl. No.: 14/612,804

(22) Filed: Feb. 3, 2015

(65) Prior Publication Data

US 2016/0223464 A1 Aug. 4, 2016

(51) Int. Cl.
*G01N 21/65* (2006.01)
*B01L 3/00* (2006.01)

(52) U.S. Cl.
CPC ...... *G01N 21/658* (2013.01); *B01L 3/502715* (2013.01); *B01L 2300/0654* (2013.01); *B01L 2300/0816* (2013.01); *B01L 2300/0877* (2013.01)

(58) Field of Classification Search
CPC  G01N 21/658; G01N 21/65; B01L 3/502715; B01L 3/5027; B01L 3/502; B01L 3/50
USPC ............................ 422/503, 502, 501, 500, 50
See application file for complete search history.

(56) References Cited

U.S. PATENT DOCUMENTS

| | | |
|---|---|---|
| 4,802,761 A | 2/1989 | Bowen |
| 4,834,494 A | 5/1989 | DeMeritt et al. |
| 4,997,278 A | 3/1991 | Finlan et al. |
| 5,332,690 A | 7/1994 | Cho et al. |
| 5,416,624 A | 5/1995 | Karstensen |
| 5,485,277 A | 1/1996 | Foster |
| 5,502,560 A | 3/1996 | Anderson et al. |
| 5,610,708 A | 3/1997 | Anderson et al. |
| 5,729,641 A | 3/1998 | Chandonnet et al. |
| 5,835,645 A | 11/1998 | Jorgenson et al. |
| 5,858,799 A | 1/1999 | Yee et al. |
| 5,864,397 A | 1/1999 | Vo-Dinh |
| 5,898,503 A | 4/1999 | Keller et al. |
| 5,912,456 A | 6/1999 | Melendez et al. |
| 5,953,118 A | 9/1999 | O'Rourke et al. |
| 6,111,248 A | 8/2000 | Melendez et al. |
| 6,191,847 B1 | 2/2001 | Melendez et al. |
| 6,466,323 B1 | 10/2002 | Anderson et al. |

OTHER PUBLICATIONS

Roulet, Jean-Christophe et al, Performance of an Integrated Microoptical System for Fluorescence Detection in Microfluidic Systems, Anal. Chem, 2002, 74, 3400-3407.*
Fan, Y. J. et al, Three dimensional microfluidics with embedded microball lense for parallel and high throughput multicolor fluorescence detection, Biomicrofluidics, 7, 2013, 044121-1 to 044121-13.*
E. Kretschmann, H. Raether, Z. Naturf A, 23, pp. 2135, 1968.
S.R. Karlsen, K.S. Johnston, R.C. Jorgenson, S.S. Yee, Simultaneous determination of refractive index and absorbance spectra of chemical samples using surface plasmon resonance, Sensors and Actuators B, 24-25, pp. 747-749, 1995.
F. Aussenegg, A. Leitner, Z. Zhao, Enhanced sensitivity, of dye monolayers as chemical sensors by electrodynamic interaction with a smooth metal surface, Sensors and Actuators B, 17, pp. 171-174, 1994.
H. Kano, S. Kawata, Surface-Plasmon Sensor for Absorption-Sensitivity Enhancement, Applied Optics, 33(22), pp. 5166-5170, 1994.
L. Fägerstam, Å Frostell-Karlsson, R. Karlsson, B. Persson, I. Rönnberg, Biospecific interaction analysis using surface plasmon resonance detection applied to kinetic, binding site and concentration analysis, J. of Chrom., 597, pp. 397-410, 1992.
R. Karlsson, A. Michaelsson, L. Mattsson, Kinetic analysis of monoclonal antibody-antigen interactions with a new biosensor based analytical system, J. of Immunological Methods, 145, pp. 229-240, 1991.
D. Altschuh, M. Dubs, E. Weiss, G. Zeder-Lutz, M. Regenmortel, Determination of Kinetic Constants for the Interaction between a Monoclonal Antibody and Peptides Using Surface Plasmon Resonance, Biochemistry, 31, pp. 6298-6304, 1992.
B. Liedberg, C. Nylander, I. Lundstrem, Surface Plasmon Resonance for Gas Detection and Biosensing, Sensors and Actuators, 4, pp. 299-304, 1983.
K. Matsubara, S. Kawata, S. Minami, Optical chemical sensor based on surface plasmon measurement, Applied Optics, 27, pp. 1160-1163, 1988.
M. Niggemann, A. Katerkamp, M. Pellmann, P. Bolsmann, J. Reinbold, K. Cammann, Remote sensing of tetrachloroethene with a micro-fibre optical gas sensor based on surface plasmon resonance spectroscopy, Sensors and Actuators B, 34, pp. 328-333, 1996.
M.J. Jory, P.S. Vukusic, J.R. Sambles, Development of a prototype gas sensor using surface plasmon resonance on gratings, Sensors and Actuators B, 17, pp. 203-209, 1994.
H. Morgan, D.M. Taylor, A surface plasmon resonance immunosensor based on the streptavidin-biotin complex, Biosensors and Bioelectronics, 7, pp. 405-410, 1992.
A.H. Severs, R.B.M. Schasfoort, M.H.L. Salden, An immunosensor for syphilis screening based on surface plasmon resonance, Biosensors and Bioelectronics, 8 pp. 185-189, 1993.
C. Jung, S. Yee, K. Kuhn, Electro-optic polymer light modulator based on surface plasmon resonance, Applied Optics, 34, pp. 946-949 1995.

(Continued)

*Primary Examiner* — Christine T Mui
(74) *Attorney, Agent, or Firm* — Patent Law of Virginia, PLLC; Brian J. Teague

(57) ABSTRACT

A micro-fluidic chip comprises a chip base, a hemispherical or curved lens, and a securing portion. The chip base has a flow cell and a micro-fluidic channel defined therein. The micro-fluidic channel is fluidly connected to the flow cell to deliver fluid to and from the flow cell, respectively via a fluid input port and a fluid output port. The lens has an apex and a base. The apex is positioned within the flow cell. The securing portion is affixed to the chip base such that the lens is sandwiched between the chip base and the securing portion. The securing portion has a circular cavity defined therein in a surface adjacent the chip base, for receiving the base of the lens. The securing portion further has separate light input and output channels to allow light in and out, respectively, of the circular cavity and the lens.

23 Claims, 4 Drawing Sheets

(56) References Cited

OTHER PUBLICATIONS

M. Manuel Vidal, R. Lopez, S. Alegret, J. Alonso-Chamarro, I. Garces, J. Mateo, Determination of probable alcohol yield in musts by means of an SPR optical sensor, Sensors and Actuators B, 11, 455-459, 1993.
H. Bruijn, R. Kooyman, J. Greve, Applied Optics, 32(13), pp. 2426-2430, 1995.
F. Schmitt, K. Wolfgang, J. of Biophysics, 60, pp. 716-720, 1991.
R.E. Dessy, W.J. Bender, Analytical Chemistry, 66, pp. 963-970, 1994.
J.R. Castillo, G. Cepria, S. de Marcos, J. Galban, J. Mateo, E. Ruiz, Sensors and Actuators A, 37-38, pp. 582-586, 1993.

\* cited by examiner

MICRO-FLUIDIC SURFACE PLASMON RESONANCE CHIP

FIELD OF THE INVENTION

The present invention relates generally to a device for surface plasmon resonance spectroscopy, and particularly relates to a micro-fluidic chip for surface plasmon resonance spectroscopy.

BACKGROUND OF THE DISCLOSURE

Surface plasmon resonance (SPRS) is an optical phenomenon that occurs when light is cast at a certain angle onto a prism that has upon one surface a thin layer of conductive coating. The coating could comprise of one or more conductive or dielectric layers. When the light is shined into the prism at a particular "critical angle," the light may totally internally reflect within the prism so that it does not escape that side of the prism. The critical angle depends upon the characteristics of the prism, the layer(s), or the environment surrounding the entire structure. This is caused by the interaction between light or other electromagnetic radiation and several different types of materials, usually comprising a dielectric material and a conductive material arranged in a multi-layer stack of thin films. Light that totally internally reflects within a coated prism forms an electromagnetic wave that propagates along the conductive (i.e., metal) layer boundary. This wave is known as a surface plasmon. The surface plasmon wave is optically excited at the interface between a conductor or semiconductor, e.g., a metal surface and a dielectric. For excitation of these surface plasmons a light source is needed.

Surface plasmon resonance spectroscopy (SPRSS) is a unique optical surface sensing technique with applications in a variety of disciplines. SPRS can be used to probe refractive index changes that occur within the immediate vicinity of a sensor surface. Thus, any physical phenomenon which alters the refractive index will elicit a response. Initial applications of SPRS involved the investigation of optical properties inherent to thin metal films. From these studies, SPRS has expanded and is used in of variety of applications including: absorbance measurements, biokinetic and biosensing techniques, bulk liquid measurements, gas detection, immunosensing, light modulation, process analytics, spectrometers, SPRS microscopy, refractive index measurements, SPRS polarization fibers, and thin film characterization. In recent years, the development of SPRS has been directed toward biosensing techniques. However, SPRS has not been limited to this field, for it has been used extensively in electrical engineering, chemistry, theoretical physics, and experimental optics.

Surface plasmon Resonance spectroscopy is a powerful technique to measure biomolecular interactions in real-time in a label free environment. While one of the interactants is immobilized to the sensor surface, others are free in solution and pass over the surface. Association and dissociation between the immobilized and free interactants is measured in arbitrary units and displayed in a graph called the sensorgram. Biomolecular Interaction Analysis is applicable to a variety of molecular pairs including interactions between DNA-DNA, DNA-protein, lipid-protein and hybrid systems of biomolecules. Non-biological surfaces can also be investigated.

BRIEF SUMMARY OF THE DISCLOSURE

In one embodiment of the invention, a micro-fluidic chip comprises a chip base, an embedded hemispherical or curved lens, and a securing portion affixed to the chip base such that the lens is sandwiched between the chip base and the securing portion. The chip base has a flow cell defined therein and a micro-fluidic channel defined therein. The micro-fluidic channel is fluidly connected to the flow cell to deliver fluid to and from the flow cell. The chip base further has a fluid input port fluidly connected to the micro-fluidic channel to deliver fluid thereto, and a fluid output port fluidly connected to the micro-fluidic channel to remove fluid therefrom. The embedded hemispherical or curved lens has an apex and a base, the apex being positioned within the flow cell. The securing portion has a circular cavity defined therein in a surface adjacent the chip base. The circular cavity receives the base of the lens. The securing portion further has separate light input and output channels defined therein in a surface opposite the chip base. Each light channel is at least partially open to the circular cavity to allow light in and out, respectively, of the circular cavity and the lens.

The light input channel and the light output channel may be spaced a distance apart relative to a diameter of the lens necessary to give rise to a surface plasmon resonance when light is introduced to the lens via the light input channel.

The micro-fluidic chip may comprise a unitary device that is separate from any chip reader or optical reader for performing surface plasmon resonance spectroscopy.

The flow cell may have a generally circular shape.

The flow cell may be fluidly connected to the micro-fluidic channel at opposing sides.

A circular opening to the flow cell may be defined in the chip base, such that the apex of the lens is seated in the circular opening.

The micro-fluidic chip may further comprise a light source supplying light to the lens via the light input channel, and a light receiver receiving light from the lens via the light output channel.

The fluid may comprise buffers and reagents.

The apex of the lens may be coated with gold or silver.

The micro-fluidic chip may further comprise a plurality of flow cells defined in the chip base, a plurality of micro-fluidic channels defined in the chip base, a plurality of fluid input ports, a plurality of fluid output ports, and a plurality of hemispherical or curved lenses. Each lens may have an apex and a base, the apex of each being positioned within a respective flow cell. Each lens may be sandwiched between the chip base and the securing portion. Each micro-fluidic channel may be fluidly connected to a respective one of the plurality of flow cells to deliver fluid to and from the respective flow cell. Each fluid input port may be fluidly connected to a respective one of the plurality of micro-fluidic channels to deliver fluid thereto. Each fluid output port may be fluidly connected to a respective one of the plurality of micro-fluidic channel to remove fluid therefrom. A plurality of circular cavities may be defined in the securing portion in the surface adjacent the chip base, each circular cavity to receive the base of a respective lens. A plurality of separate light input and output channels may be defined in the securing portion in the surface opposite the chip base, each light channel at least partially open to a respective circular cavity to allow light in and out, respectively, of the respective circular cavity and the respective lens.

A length of each micro-fluidic channel may be selected such that the fluid is delivered to each flow cell simultaneously.

Every micro-fluidic channel may have an equal length between its respective input port and its respective flow cell.

In addition to the micro-fluidic chip, as described above, other aspects of the present invention are directed to corresponding methods for performing surface plasmon resonance spectroscopy using the micro-fluidic chip of embodiments of the invention.

BRIEF DESCRIPTION OF THE SEVERAL VIEWS OF THE DRAWINGS

The foregoing summary, as well as the following detailed description of the disclosure, will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities shown. In the drawings.

DETAILED DESCRIPTION OF THE DISCLOSURE

Figure 1:
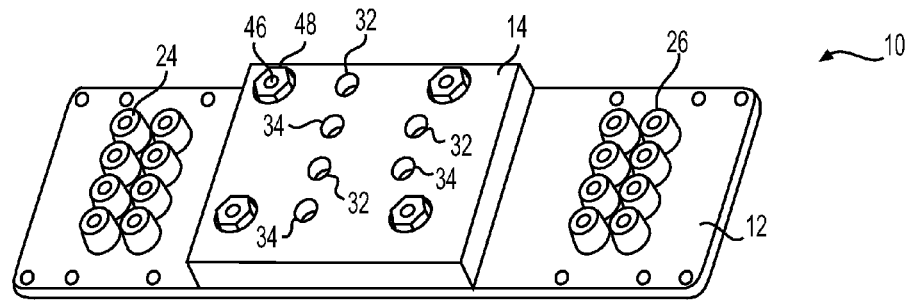
FIG. 1 is a perspective top view of a micro-fluidic chip, in accordance with embodiments of the present

Certain terminology is used in the following description for convenience only and is not limiting. The words "lower," "bottom," "upper," and "top" designate directions in the drawings to which reference is made. The words "inwardly," "outwardly," "upwardly" and "downwardly" refer to directions toward and away from, respectively, the geometric center of the device, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

Embodiments of the invention are directed to a micro-fluidic chip which has a lens mounted inside the chip in a particular manner, in conjunction with fluidics and optics enabling it to perform a SPRS spectroscopy experiment. This arrangement can be extended to present a series of such lens in similar geometry to perform in real time to produce desired SPRS data. Embodiments of the invention are not limited to using three channels, as illustrated. Embodiments of the invention can include as many channels as can fit on a chip of this size or a bigger chip. Embodiments of the invention with multiple channels may be used to perform several different assays or the same assay on multiple samples simultaneously.

Surface plasmon resonance technology offers an opportunity to develop highly sensitive, specific, and cost effective diagnostic test platforms for detection of disease-causing agents. Such platform have tremendous scope of use as POC (point of care) systems or other customized dedicated devices monitoring any specific disease condition. Such a platform will also serve a great tool for the research and development laboratories for target identification and validation. Blood-based screening tests for cancer markers have a greater market potential than more invasive tissue-based and nucleic acid based assays.

The present invention accordingly aims to achieve at least one, more or combinations of the following objectives:
a) A low cost and compact design system inherent in the technical design of embodiments of the invention.
b) Taking advantage of the geometry of the system, embodiments of the invention offer an excellent way to perform enzyme-linked immunosorbent assays (ELISAs). Conventionally, ELISA are performed by adding a color developing reagent at the end of an antigen-antibody reaction to access the binding. Embodiments of the invention will bypass that and will enable ELISAs to be performed in the absence of any color developing reagents, thereby requiring very small developing and equilibration times. This may cut assay time from 4 hours (in some cases overnight) to less than ten minutes. Such reductions of processing time can be achieved conveniently simply by adding more channels. It is believed that there is no other technology or SPRS system which offers this advantage, which is made possible by the chip design and vertical optical geometry of embodiments of the invention.

Figure 2:
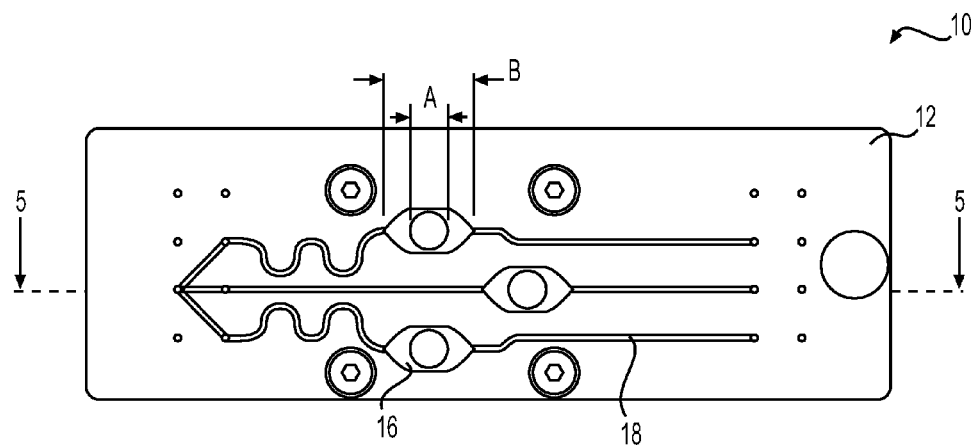
FIG. 2 is a bottom view of the micro-fluidic chip of FIG. 1.
Figure 3:
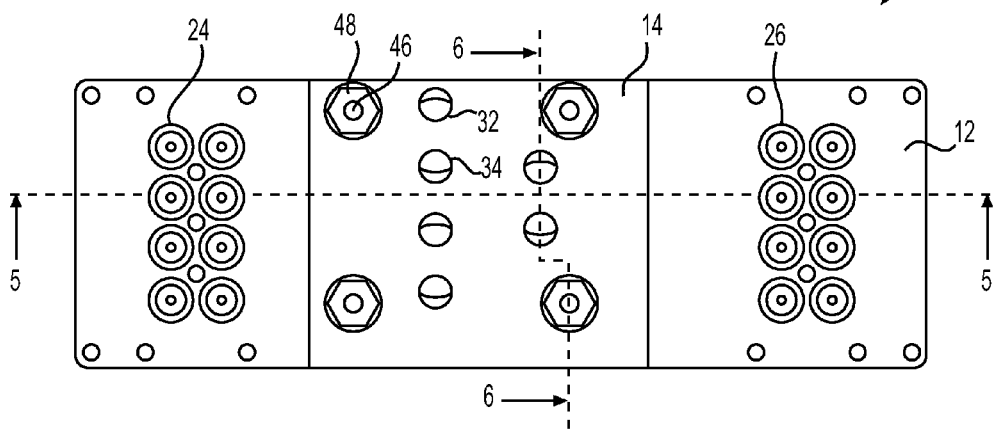
FIG. 3 is a top view of the micro-fluidic chip of FIG. 1.

Referring now to the figures, wherein like numerals indicate like elements throughout, there is illustrated a micro fluidic chip 10 to perform SPRS spectroscopy. The micro fluidic chip 10 of embodiments of the invention comprises a base 12 and a securing portion 14 (also termed a chip clip) affixed thereto. One or more flow cells 16 (three are illustrated) are defined in the base 12 of the micro fluidic chip 10, along with one or more micro-fluidic channels 18 (three are illustrated). The micro-fluidic channels 18 are fluidly connected to the flow cells 16 to deliver fluid (also termed a "buffer") to and from the flow cells 16. In the illustrated embodiment, the flow cells 16 are generally circular in shape, and the flow cells are fluidly connected to the respective micro-fluidic channel at opposing sides as seen in FIG. 2 (the circular portion seen in FIG. 2 is the flow cell 16; the flow cell may be surrounded by a small void (which is hexagonal in FIG. 2, but may be of any other suitable shape) or flow channels can directly deliver fluids to and from the flow cell). In the illustrated embodiment, the flow cells are 3.3 mm (diameter) (dimension A in FIG. 2) by 0.35 mm (depth) (dimension F in FIG. 7). The fluid may comprise, for example, buffers and reagents useful to perform an SPRS assay. The micro fluidic chip 10 of embodiments of the invention further comprises one or more fluid input ports 24 (eight are illustrated), (more or fewer ports can be used depending upon how many flow cells and how many different reagents for fluidic treatments are needed), each fluidly connected to one, more than one, or none of the micro-fluidic channels to deliver fluid to the flow cells. Some input ports may be connected to multiple channels, and some channels may be connected to multiple input ports to enable further possibilities of using combinations of different fluidics, and to enable inclusion and exclusion from certain fluidic treatment of the chip surface. The micro fluidic chip 10 of embodiments of the invention further comprises one or more fluid output ports 26 (eight are illustrated), each fluidly connected to one, more than one, or none of the micro-fluidic channels to remove fluid from the flow cells. (Some output ports in the illustrated embodiment are not connected to a channel and are therefore non-working ports. In some situations, manufacturing the chip with a set number of ports (input and/or output) is easier even if some of the ports will not be used.) In this regard, the fluid is delivered to the chip 10 via one or more of the input ports, travels down one or more of the channels to one or more of the flow cells, continues to travel from the flow cells down one or more of the channels to one or more of the output ports, and the fluid is removed from the chip via one or more of the output ports. While the ports 24 on the left side of FIG. 1 are described herein as input ports and the ports 26 on the right side of FIG. 1 are described herein as output ports for convenience, either group of ports could function as input ports and either group of ports could function as output ports. If the ports 24 on the left side of FIG. 1 were used as output ports, it would be possible to collect all of the fluid to be removed from a single port, as all three channels converge to a single port (see the left side of FIG. 2). Typical flow through a system of embodiments of the invention is 3 to 20 microliters per minute (uL/min). The volume of the reagents consumed per assay depends upon the time taken to finish a particular experiment. For example, an assay taking 100 minutes to complete can consume 300 to 500 uL of the reagent depending upon the flow rate.

Figure 4:
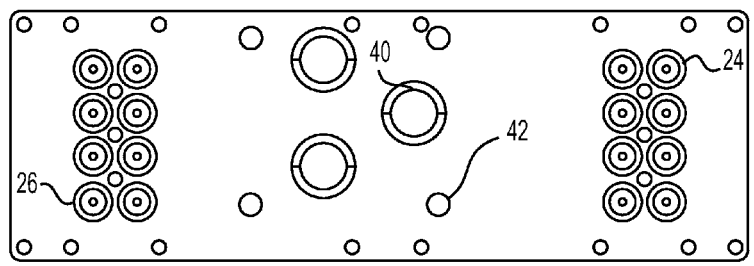
FIG. 4 is a top view of the micro-fluidic chip of FIG. 1, without the securing portion.
Figure 5:
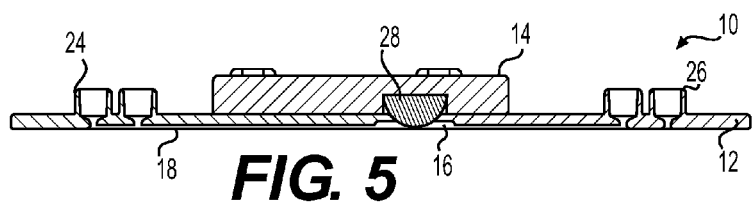
FIG. 5 is a cross-sectional side view of the micro-fluidic chip of FIG. 1, along line 5-5 shown in FIGS. 2 and 3.
Figure 6:
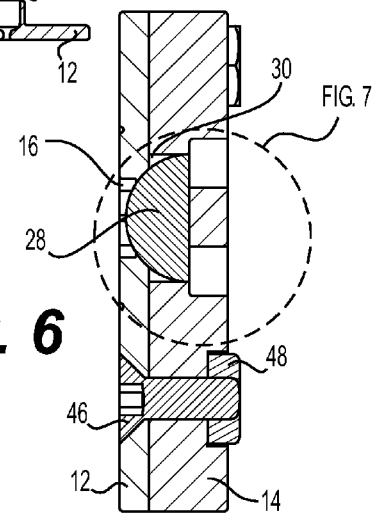
FIG. 6 is a cross-sectional end view of the micro-fluidic chip of FIG. 1, along line 6-6 shown in FIG. 3.
Figure 7:
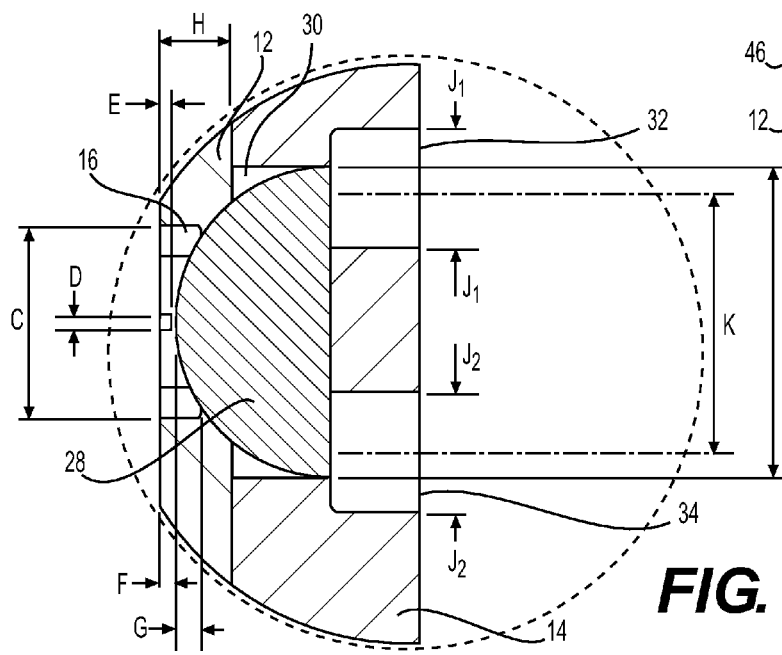
FIG. 7 is a close-up view of a portion of the cross-sectional end view of FIG. 6.
Figure 8:
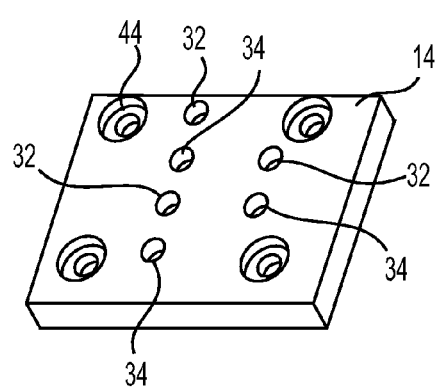
FIG. 8 is a top perspective view of the securing portion of the micro-fluidic chip of FIG. 1.
Figure 9:
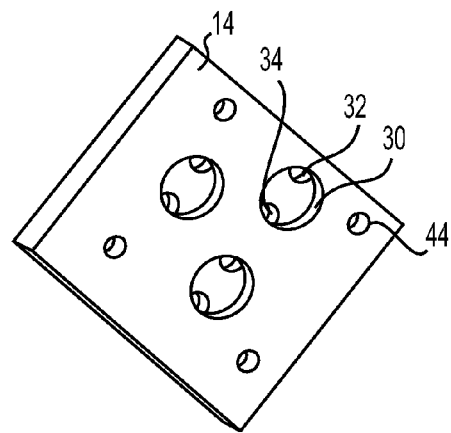
FIG. 9 is a bottom perspective view of the securing portion of the micro-fluidic chip of FIG. 1.
Figure 10:
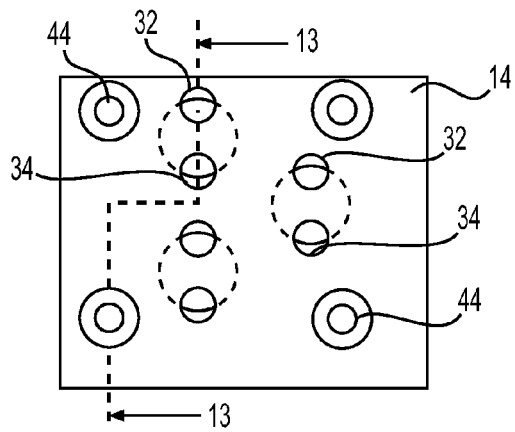
FIG. 10 is a top view the securing portion of the micro-fluidic chip of FIG. 1.
Figure 11:
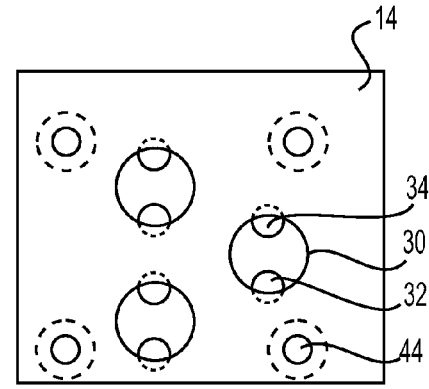
FIG. 11 is a bottom view of the securing portion of the micro-fluidic chip of FIG. 1.
Figure 12:
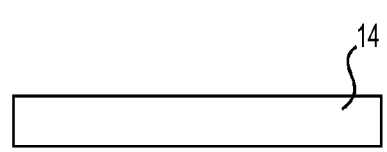
FIG. 12 is an end view of the securing portion of the micro-fluidic chip of FIG. 1.
Figure 13:
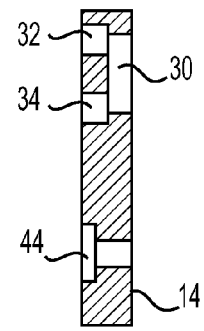
FIG. 13 is a cross-sectional end view of the securing portion of the micro-fluidic chip of FIG. 1, along line 13-13 shown in FIG. 10.

The micro fluidic chip 10 of embodiments of the invention further comprises a hemispherical or curved lens 28 having an apex and a base. The apex protrudes through and is seated in a circular opening 40 defined in the chip base 12 (the opening 40, seen in FIG. 4, has a diameter of 3.289 mm (dimension A in FIG. 2) and has a curved wall that cooperates with the curved lens to enable the lens to be properly seated), such that the apex of the lens is positioned within the flow cell 16, as seen in FIGS. 5-7. The apex of the lens is coated with an appropriate medium to perform SPRS, such as gold or silver. The securing portion 14 is affixed to the chip base 12 such that the lens 28 is sandwiched between the chip base 12 and the securing portion 14, as seen in FIGS. 5-7. The securing portion has one or more circular cavities 30 (one for each lens), defined in the surface that is adjacent the chip base when affixed, each cavity 30 is to receive the base of a corresponding lens (this can be seen in FIGS. 5-7). The securing portion 14 further has separate light input and output channels 32, 34, respectively, defined in the surface that is opposite the chip base when affixed. Each light channel is at least partially open to the circular cavity 30 to allow light in and out, respectively, of the circular cavity 30 and the lens 28. As seen in FIGS. 3, 9-11, and 13, the light input channel 32 partially overlaps the circular cavity 30 and the light output channel 34 partially overlaps the circular cavity 30. The securing portion 14 is affixed to the base 12 via screws 46 and corresponding nuts 48 inserted through corresponding holes 42 in the base and holes 44 in the securing portion.

Figure 14:
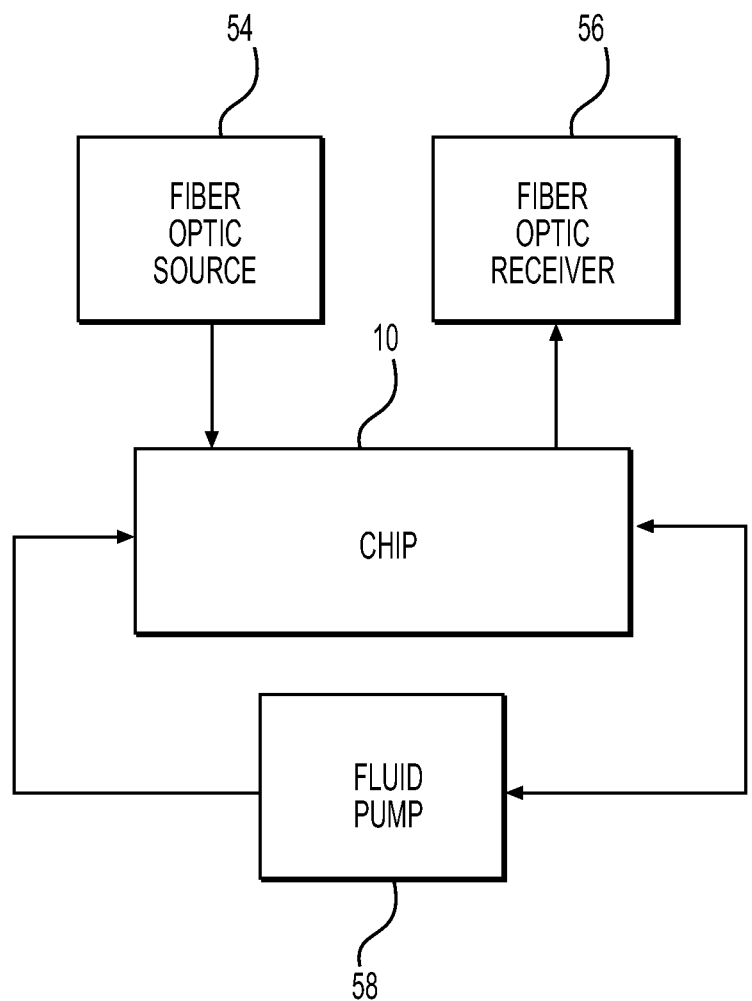
FIG. 14 is a block diagram of a system for surface plasmon resonance spectroscopy using the micro-fluidic chip of FIG. 1.

The lens 28 is housed and positioned inside the chip 10 in such a way that the apex of the lens becomes a part of a micro-fluidic flow cell 16 (which is, as described above, connected to micro-fluidic channels 18 to control input and output of the liquid inside the cell). The base of the lens seats inside a securing portion (also termed a chip clip) having two precisely drilled light channels 32, 34 for, respectively, input of fiber optic light from a fiber optic light source 54 and output of fiber-optic light to a fiber optic receiver 56. The light source and receiver may be part of a chip reader, illustrated in the block diagram of FIG. 14, which may be a separate module which has capability of reading this chip. Such a chip reader may also comprise a pump 58 for pumping of fluidics into the chip (via the input ports, as discussed above).

The micro-fluidic chip illustrated herein has eight input and output ports (which may be, for example, mini luer adapters) to handle input and output of micro fluidics. The micro-fluidic chip may have single lens or a plurality of lenses and micro fluidic channels formed by a plurality of connected geometrical structures having a predetermined depth. The micro fluidic channels have an inlet and an outlet for inputting the fluidics and outputting the same respectively using external fluidic pumps. The micro-fluidic chip illustrated herein has three micro fluidic channels (seen in FIG. 2). Each of the three micro-fluidic channels is connected to a separate output port. Each of the three micro-fluidic channels could be connected to a common input port or connected to three different input ports (both are illustrated in FIG. 2). As such, it is possible to flow buffer through these channels separately (using the separate input ports in the column closer to the center of the chip) or in unison (using the common input port in the column closer to the edge of the chip).

The paths of the channels may be selected so that the length of all the channels remains same, such that when a buffer is commonly introduced to all the channels the buffer takes an equal amount of time to reach the lens apex in all the flow cells. In the illustrated embodiment, this is accomplished by having the peripheral (i.e., top and bottom in FIG. 2) channels be serpentine.

In the illustrated embodiment of the invention, the lenses are embedded inside the chip clip in a certain geometry. This is significant as the lens sits tightly fixed in the chip clip and is geometrically positioned with regards to optics and fluidics such that when a light source shines light on its base, its position creates an SPRS phenomenon. In the illustrated embodiment of the invention, a 6.35 mm lens (measured as the diameter of the base) is used (a size very suitable for an ELISA plate well), which is housed in a 6.4 mm lens seat (i.e., circular cavity 30) (dimension I in FIG. 7) on the clip. For a chip of this geometry, the two light channels 32, 34 have a 2.49 mm diameter (dimensions J1 and J2 in FIG. 7), and the distance between centers of these light channels is maintained at 5.52 mm (dimension K in FIG. 7). On the apex side of the chip, micro-fluidic channels having a depth of 0.2 mm (dimension E in FIG. 7) and height of 0.3 mm (dimension D in FIG. 7) are used to pump buffer in and out of these flow cells. The apex of the lens projects into 0.46 mm into the flow cell (dimension G in FIG. 7). The distance between the apex of the lens and the bottom of the chip is 0.35 mm (dimension F in FIG. 7). In the illustrated embodiment, the base is 75.5 mm by 25.5 mm by 1.5 mm (dimension H in FIG. 7). The securing portion is 30 mm by 25.5mm by 4 mm. While the positional relationships between the flow cells, the lenses, the circular cavities, and the light channels are critical, the location on the base and securing portion is less important (as long as the above-described positional relationships (or other suitable positional relationships that may be derived) are maintained).

A suitable external pumping device (such as pump 58 of FIG. 14) is used to flow buffer at 20 uL/minute. This could vary as per need of the experiment. One of the most important features of this system is that the positioning of the lens, flow cell, and placement of the fiber optic channels. These are mathematically calculated and light must strike the lens at certain point in order for it to do a total internal reflection and is collected back from the other channel. For example lens used here is 6.35 mm diameter and has a certain mathematical relationship to angle at which light is shined on it, however lens of smaller sizes or bigger sizes can as well be used and thus the channel diameter and distances from the center can vary accordingly and can be calculated.

The illustrated design allows the base of the lens to contact fiber optic components of a light source and reader to input light and measure the output. The lens is held in place water tight through a precisely engineered clip.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

That which is claimed:

1. A micro-fluidic chip comprising:
    a chip base having a flow cell defined therein and a micro-fluidic channel defined therein, the micro-fluidic channel being fluidly connected to the flow cell to deliver fluid to and from the flow cell, the chip base further having a fluid input port fluidly connected to the micro-fluidic channel to deliver fluid thereto, and the chip base further having a fluid output port fluidly connected to the micro-fluidic channel to remove fluid therefrom;
    a hemispherical or curved lens having an apex and a base, the apex being positioned within the flow cell; and
    a securing portion affixed to the chip base such that the lens is sandwiched between the chip base and the securing portion, the securing portion having a circular cavity defined therein in a surface adjacent the chip base, the circular cavity to receive the base of the lens, the securing portion further having separate light input and output channels defined therein in a surface opposite the chip base, each light channel on a base sdie of the lens and at least partially open to the circular cavity such that the light input channel allows light into the circular cavity and the base of the lens and such that the light output channel allows light out of the circular cavity and the base of the lens.

2. The micro-fluidic chip of claim 1, wherein the light input channel and the light output channel are spaced a distance apart necessary to give rise to a surface plasmon resonance when light is introduced to the lens via the light input channel.

3. The micro-fluidic chip of claim 1, wherein the micro-fluidic chip comprises a unitary device that is separate from any chip reader or optical reader for performing surface plasmon resonance spectroscopy.

4. The micro-fluidic chip of claim 1, wherein the flow cell has a circular shape.

5. The micro-fluidic chip of claim 4, wherein the flow cell is fluidly connected to the micro-fluidic channel at opposing sides.

6. The micro-fluidic chip of claim 4, wherein a circular opening to the flow cell is defined in the chip base, such that the apex of the lens is seated in the circular opening.

7. The micro-fluidic chip of claim 1, further comprising:
    a light source supplying light to the lens via the light input channel; and
    a light receiver receiving light from the lens via the light output channel.

8. The micro-fluidic chip of claim 1, wherein the fluid comprises buffers and reagents.

9. The micro-fluidic chip of claim 1, wherein the apex of the lens is coated with gold or silver.

10. The micro-fluidic chip of claim 1, further comprising:
    a plurality of flow cells defined in the chip base;
    a plurality of micro-fluidic channels defined in the chip base;
    a plurality of fluid input ports;
    a plurality of fluid output ports; and
    a plurality of hemispherical or curved lenses, each having an apex and a base, the apex of each being positioned within a respective flow cell, each lens sandwiched between the chip base and the securing portion;
    wherein each micro-fluidic channel is fluidly connected to a respective one of the plurality of flow cells to deliver fluid to and from the respective flow cell;
    wherein each fluid input port is fluidly connected to a respective one of the plurality of micro-fluidic channels to deliver fluid thereto;
    wherein each fluid output port is fluidly connected to a respective one of the plurality of micro-fluidic channel to remove fluid therefrom;
    wherein a plurality of circular cavities are defined in the securing portion in the surface adjacent the chip base, each circular cavity to receive the base of a respective lens; and
    wherein a plurality of separate light input and output channels are defined in the securing portion in the surface opposite the chip base, each light channel on a base side of its respective lens and at least partially open to a respective circular cavity such that each light input channel allows light into the respective circular cavity and the base of the respective lens and such that each light output channel allows light out of the circular cavity and the base of the respective lens.

11. The micro-fluidic chip of claim 10, wherein a length of each micro-fluidic channel is selected such that the fluid is delivered to each flow cell simultaneously.

12. The micro-fluidic chip of claim 10, wherein every micro-fluidic channel has an equal length between its respective input port and its respective flow cell.

13. A micro-fluidic chip comprising:
a chip base having a plurality of flow cells defined therein and a plurality of micro-fluidic channels defined therein, each micro-fluidic channel being fluidly connected to a respective flow cell to deliver fluid to and from the flow cell, the chip base further having a plurality of fluid input ports fluidly connected to a respective micro-fluidic channel to deliver fluid thereto, and the chip base further having a plurality of fluid output ports fluidly connected to a respective micro-fluidic channel to remove fluid therefrom;
a plurality of hemispherical or curved lenses, each lens having an apex and a base, the apex of each lens being positioned within a respective flow cell; and
a securing portion affixed to the chip base such that the lenses are sandwiched between the chip base and the securing portion, the securing portion having a plurality of circular cavities defined therein in a surface adjacent the chip base, each circular cavity to receive the base of a respective lens, the securing portion further having a plurality of separate light input and output channels defined therein in a surface opposite the chip base, each light channel on a base side of its respective lens and at least partially open to a respective circular cavity such that each light input channel allows light into the respective circular cavity and the base of a respective lens and such that each light output channel allows light out of the respective circular cavity and the base of the respective lens.

14. The micro-fluidic chip of claim 13, wherein the light input channel and the light output channel are spaced a distance apart necessary to give rise to a surface plasmon resonance when light is introduced to the lens via the light input channel.

15. The micro-fluidic chip of claim 13, wherein the micro-fluidic chip comprises a unitary device that is separate from any chip reader or optical reader for performing surface plasmon resonance spectroscopy.

16. The micro-fluidic chip of claim 13, wherein each flow cell has a circular shape.

17. The micro-fluidic chip of claim 16, wherein each flow cell is fluidly connected to a respective micro-fluidic channel at opposing sides.

18. The micro-fluidic chip of claim 16, wherein a circular opening to each flow cell is defined in the chip base, such that the apex of each lens is seated in a respective circular opening.

19. The micro-fluidic chip of claim 13, further comprising:
one or more light sources supplying light to each lens via a respective light input channel; and
one or more light receivers receiving light from each lens via a respective light output channel.

20. The micro-fluidic chip of claim 13, wherein the fluid comprises buffers and reagents.

21. The micro-fluidic chip of claim 13, wherein the apex of each lens is coated with gold or silver.

22. The micro-fluidic chip of claim 13, wherein a length of each micro-fluidic channel is selected such that the fluid is delivered to each flow cell simultaneously.

23. The micro-fluidic chip of claim 13, wherein every micro-fluidic channel has an equal length between its respective input port and its respective flow cell.

* * * * *